United States Patent [19]

Hwu et al.

[11] Patent Number: 5,434,277

[45] Date of Patent: Jul. 18, 1995

[54] IMPROVED METALLIC SOAPS OF FATTY ACIDS FOR USE AS PHOTOLYZING AGENTS FOR PHOTODEGRADABLE POLYMER FILMS

[75] Inventors: Herng-Dar Hwu, Taoyuan; Hung Y. Hsu, Hsinchu; Jian-Hong Chen, Hsinchu; Shu-Fang Jiang, Hsinchu, all of Taiwan

[73] Assignee: Industrial Technology Research Institute, Chutung, Taiwan

[21] Appl. No.: 22,962

[22] Filed: Apr. 2, 1993

[51] Int. Cl.⁶ .............................................. C07F 19/00
[52] U.S. Cl. .................................... 554/71; 554/72; 554/74; 554/156; 554/158; 554/194; 554/195
[58] Field of Search ................. 554/72, 74, 156, 192, 554/158, 194, 195, 71

[56] References Cited
U.S. PATENT DOCUMENTS

3,840,512  10/1974  Brackman ..................... 260/94.9
3,865,767   2/1975  Boberg .......................... 260/23 H
3,882,058   5/1975  Le Brasseur ................... 260/23 H
5,175,322  12/1992  Yoshizawa et al. ............ 554/72
5,277,832   1/1994  Gell et al. ....................... 554/156

Primary Examiner—José G. Dees
Assistant Examiner—Deborah D. Carr
Attorney, Agent, or Firm—W. Wayne Liauh

[57] ABSTRACT

A method for the preparation of metallic salts of fatty acids comprising the steps of: (a) reacting alkali hydroxide with a fatty acid in a saponification reaction to form an alkali soap; (b) reacting the alkali soap with an aqueous metallic salt solution in a double decomposition reaction to cause the production of metallic fatty acid salt; (c) performing at least one cycle of an alternating alkalinization-acidization reaction by adding an aqueous alkali hydroxide solution to the metallic fatty acid salt to raise the solution pH, followed by adding an acidic aqueous salt solution contain the same metal ions to lower the solution pH. High purity metallic salts of fatty acids can be obtained without a solvent washing step and the metallic fatty acid salts prepared from this invention can be effectively used as photolyzing agent to initiate and/or accelerate the photo-degradation of plastics.

13 Claims, 8 Drawing Sheets

IMPROVED METALLIC SOAPS OF FATTY ACIDS FOR USE AS PHOTOLYZING AGENTS FOR PHOTODEGRADABLE POLYMER FILMS

FIELD OF THE INVENTION

This invention relates to a method of preparing metallic salts of fatty acids. More particularly, this invention relates to method of preparing metallic salts of fatty acids which can be used as photolyzing agent in a photo-degradable polymer matrix and which contain very low level of unreacted residual fatty acids.

BACKGROUND OF THE INVENTION

Many prior art patents have disclosed using metallic salts as photolyzing agent for photo-degradable plastics. Examples of these patents include U.S. Pat. Nos. 3,840,512, 3,865,767, 3,882,058, in which metallic salts, including those of Ti, V, Cr, Mn, Fe, Co, Ni, Cu, of fatty acids have been disclosed as effective photolyzing agents, or the so-called photo-prodegradant, to initiate and/or accelerate a photo-degradation of various plastics. The contents of these prior art patents are herein incorporated by reference.

In U.S. Pat. No. 3,865,767 (the '767 patent), it is disclosed a "di-soap" type photolyzing agent represented by the following formula:

wherein Y is an aliphatic fatty acid having a carbon number from about 6 to about 25. In the '767 patent, it is demonstrated that when part of ligands attached to the metallic ion are substituted with aliphatic carboxylate (from the fatty acid), the resultant metallic salt achieved good compatibility with plastics and can serve as excellent photo-prodegradant. Other than their applications as photolyzing agents, metallic salts of fatty acids have also been widely used as dry hardening agents for paints and inks, lubricants for plastics and rubbers, hardening accelerators for unsaturated esters, and as stabilizers for plastics.

Presently, there are three main methods for making metallic salts of fatty acids, to wit: (1) melt method, (2) double decomposition method, and (3) exchange method. In the melt method, the fatty acid is heat-melted then directly reacted with oxides or hydroxides of metals to form metallic salts of fatty acids. The melt method requires relatively simple production facility, but has the disadvantages in that: (a) the reaction takes place at elevated temperatures of about 150° C.–200° C., thus often resulting in turning the reaction product into darkened colors; (b) it is difficult to achieve complete reaction and some reactants are likely to remain in the final metallic salt products; (c) the final products must be ground, milled and/or pulverized after the reaction, this complicates the production process and increases the production cost; and (d) metal oxides often contain a variety of metal ions, thus it is often quite difficult to obtain high purity products from the melt method.

The second method, which is the so-called "double decomposition" method, involves primarily a two-step procedure. In the first step, fatty acid is reacted with sodium hydroxide or other alkali hydroxides to form sodium soap or other alkali soaps. This step is the so-called "saponification". In the subsequent or second step, an aqueous metallic salt solution is then added to the sodium soap from the first step to form metallic salts of the corresponding fatty acid. The second method takes place at relatively low reaction temperatures, between about 60° C. to 90° C. The double decomposition method ameliorates many of the disadvantages identified with the melt method disclosed above—the metallic salts obtained therefrom maintain appropriate color, contain high purity of metal, and the reaction products are in a fine powder form. With these advantages, the double decomposition method has become the most commonly used method in the commercial production of metallic fatty acid salts.

With the increased demand on the quality, particularly purity, of the metallic fatty acid salts, however, the conventional double decomposition method no longer appears satisfactory. The problems arise in that the metallic fatty acid salts produced from the double decomposition method do not provide high purity product; they often contain large amounts of unreacted fatty acids and/or sodium or alkali soaps. This problem is illustrated in U.S.S.R. Pat. No. SU 3,795,565 (the SU '565 citation), which teaches the preparation of ferric stearate using the double decomposition method. The SU '565 citation disclosed that the double decomposition method was impossible to achieve complete reaction and that about 7–10% of sodium stearate soap would still remain in the ferric stearate product. Sodium soaps including sodium stearate often cause filtration problems in the final product; therefore, in commercial processes, it is generally necessary to convert sodium stearate back to stearic acid. U.S. Pat. No. 3,840,512 disclosed a synergistic effect between fatty acid and metallic fatty acid salt in the photo-degradation of plastics. This beneficial effect, however, often cannot be realized in actual situations, and the presence of fatty acid is indeed undesirable. Due to their low molecular weight, fatty acid molecules can easily migrate to the surface of plastics matrix in which they are initially uniformly dispersed. This often adversely affects the fabricability (such as printability, sealability, etc) of the plastics which contain these fatty acid salts additives. Also, the migration of the fatty acid molecules causes a nonuniform distribution thereof within the polymer matrix, resulting an uneven or uncontrolled rate of degradation which can be easily affected by the storage environment, storage time, or even different parts of the product. To reduce the amount of residual stearic acid, the double decomposition process is often followed by a rinsing step requiring large amounts of washing solvent. This could result in substantial increase in the production cost and adds the risks of causing serious environmental pollution problems.

The third method, which is called the exchange method, is used primarily for the production of high purity tri-valent or quadruple-valent metallic fatty acid salts. The exchange method involves using excess amounts of fatty acid and the metallic salts of alkylates or alkoxides to effectuate an exchange reaction therebetween in the presence of large amounts of solvent to produce metallic fatty acid salts and alcohols. After the reaction, unreacted residual fatty acid is washed off with solvent. Japanese Pat. Pub. Sho 62-120339 (Sho '339 citation) discloses an example of the process of preparing ferric stearate using such an exchange method. In the Sho '339 citation excessive amounts of fatty acid (stearic acid) and Fe(OCH$_3$)$_3$ were dissolved in THF to cause an exchange reaction. Ferric stearate was formed as a reaction product. Because this process involves large amounts of THF, it incurs high production cost and causes the accompanying pollution problems. Furthermore, due to the excessive amounts of fatty acid that are used as reactants, about 90% of the fatty acid was unreacted and will have to be discharged along with the solvent. This further increases the cost of the product and reduces its competitiveness.

SUMMARY OF THE INVENTION

The primary object of the present invention is to develop a method for the production of metallic salts of fatty acids that eliminates many of the problems observed in the prior art methods mentioned above. More particularly, the primary object of the present invention is to develop a cost-effective method for the production of high purity metallic salts of fatty acids using a double decomposition method followed by one or more of specialized designed alternating alkalinization-acidization cycles to effectively force unreacted residual fatty acids to subject to further reaction, thereby eliminating the need for the expensive and environmentally dissonant post-reaction solvent washing step while increasing the yield and purity of the metallic fatty acid salt products. The metallic fatty acid salts produced from the method disclosed in the present invention have desirable color, are produced in fine-powder form and can be effectively used as photolyzing agent for photodegradable polymers, while incurring no or minimum environmental pollution problems.

In the present invention, fatty acids having a carbon number between about 6 to about 25 are reacted with sodium hydroxide at temperatures between 60° C. and 90° C. to cause a saponification reaction. After a gelatinous sodium soap is produced, an aqueous metal salt solution is added to the reaction mixture. The temperature of the mixture is then controlled at about 60° C. and 90° C. to initiate the double decomposition reaction which causes metallic fatty acid salts to be formed. After the reaction, the metallic fatty acid salts are filtered to remove their water content. Then sodium hydroxide solution is added to cause a saponification reaction converting the unreacted fatty acids into sodium soaps. This is the first part of the alternating alkalinization-acidization cycle of the present invention, during which the solution pH is maintained above 7 (preferably between 7-10). The temperature of the mixture is again raised when necessary until it reaches the reaction temperature of 60° C. and 90° C. An acidic aqueous metallic salt solution is then added to the mixture to cause a double decomposition reaction between the saponified sodium soap and the metallic solution. This is the second part of the alternating alkalinization-acidization cycle, during which the solution pH is maintained below 7 (preferably between 2-7) to facilitate the conversion of residual fatty acids into metallic fatty acid salts.

After the completion of one cycle of the alternating alkalinization-acidization reaction as described hereinabove, a substantial portion of the residual fatty acids will have been converted to metallic fatty acid salts and thus removed. However, additional cycles of the alternating alkalinization-acidization reaction can be administered to cause a new sequence of saponification-double decomposition reaction in the reaction product and further reduce the amount of residual fatty acid contained therein.

In summary, the present invention discloses a method that utilizes one or more alternating alkalinization-acidization reaction cycles to effectively reduce the amount of unreacted residual fatty acid and improve the reaction yield and purity of metallic fatty acid salts. The alternating alkalinization-acidization reaction cycle is achieved by alternating the solution pH, i.e., first using sodium hydroxide to effectuate alkalinization and then using the inherent acidity of the metallic salt solution to cause acidization. Since no organic solvent is required in the removal of the fatty acid, this process offers an option that is not only more cost-effective but is much more environmentally compatible than any of the prior art processes. The number of cycles of the alternating alkalinization-acidization reaction can be adjusted to control the amount the residual fatty acid allowed to be present in the final product. It can also determine the number of aliphatic carboxylate ligands (from fatty acid) to be attached to the metallic ion. Our studies indicate that three of such alternating alkalinization-acidization reaction cycles are generally adequate to achieve satisfactory results.

DETAILED DESCRIPTION OF THE PREFERRED EMBODIMENTS

The following examples provide detailed descriptions of preferred embodiments of the present invention which are provided to enable those skilled in the art to practice the same. It should be noted that these examples are presented for purposes of illustration and description and that the invention is in not intended to be limited to the precise form or forms disclosed.

EXAMPLE 1: PREPARATION OF FERRIC STEARATE 10 grams of sodium hydroxide was dissolved in 500 grams of water in a reaction bath. 75 grams of stearic acid (molecular weight=204) was added the solution. The solution was heated to a temperature of 90° C. to achieve a complete saponification of the stearic acid.

The reaction product was a transparent gelatinous sodium stearate soap. 222 ml of ferric chloride solution (0.4M) was added to the sodium soap solution to initiate the double decomposition reaction. After the reaction product, which appeared in the form of a reddish suspending agglomerate, was formed, water in the reaction bath was removed via filtration. This completes the initial portion of the synthesis reaction.

156 ml of 0.4M sodium hydroxide and 344 ml water were added into the reaction bath, which was then stirred and heated until its temperature reached 90° C. to effectuate a saponification of the unreacted residual stearic acid in the reaction product. Then 55 ml of acidic 0.4 ferric chloride solution was added to the reaction bath to cause additional metallic stearic acid salt to be formed which again was floating in the solution. This completed the first cycle of the alternating alkalinization-acidization reaction.

Two more cycles of the alternating alkalinization-acidization reaction were performed on the reaction products. The second cycle comprised the steps of adding 93.6 ml of 0.4M sodium hydroxide solution to cause saponification reaction, followed by the addition 33 ml of 0.4M ferric chloride to cause double decomposition. In the third or final cycle, 50 ml of 0.4M sodium hydroxide solution was added to cause saponification, followed by the addition of 18 ml of 0.4M ferric chloride solution to complete the entire alternating alkalinization-acidization reaction process.

Figure 1:
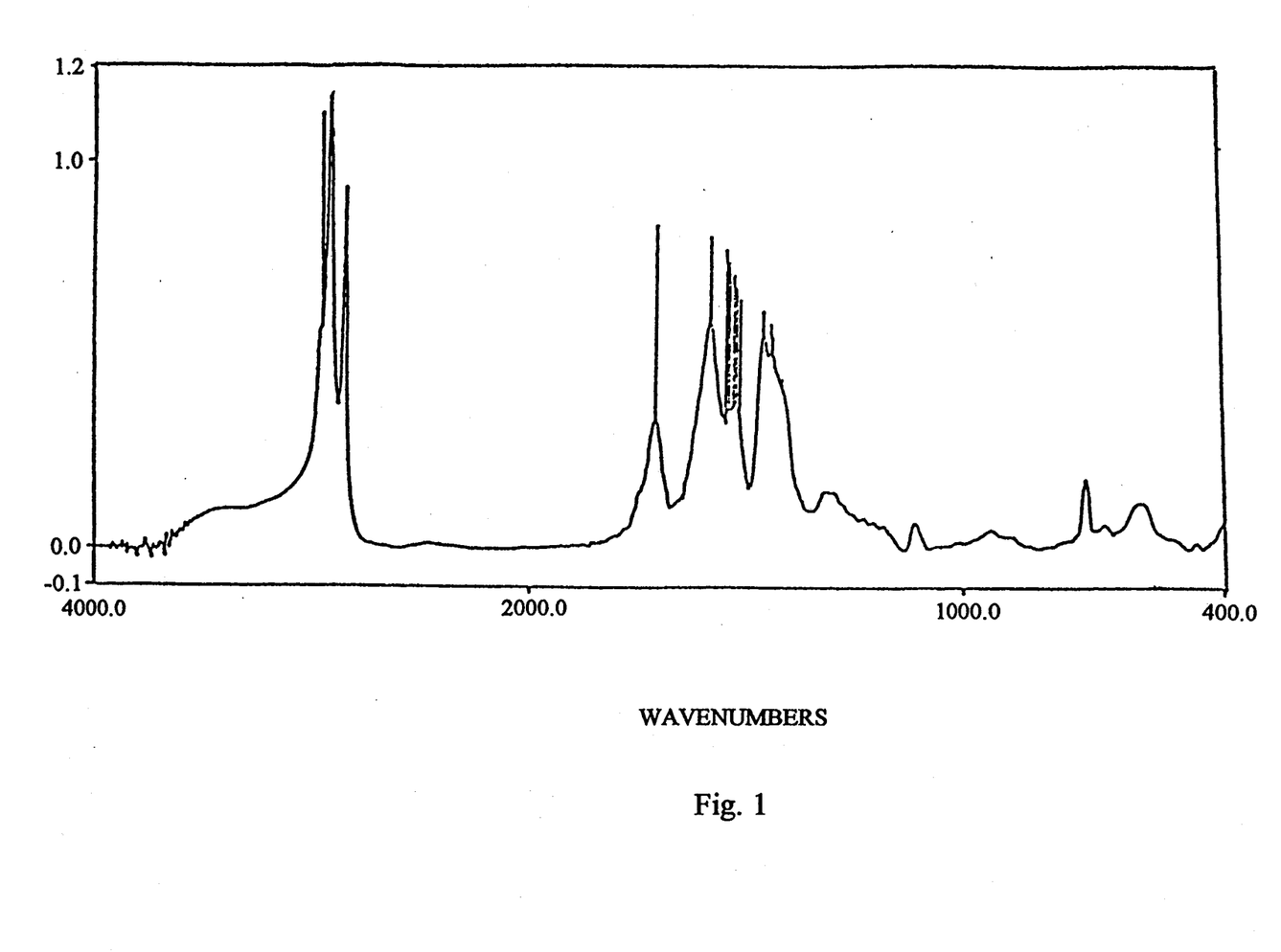
FIG. 1 is an FTIR spectrum of ferric stearate before the alternating alkalinization-acidization reaction of the invention.
Figure 2:
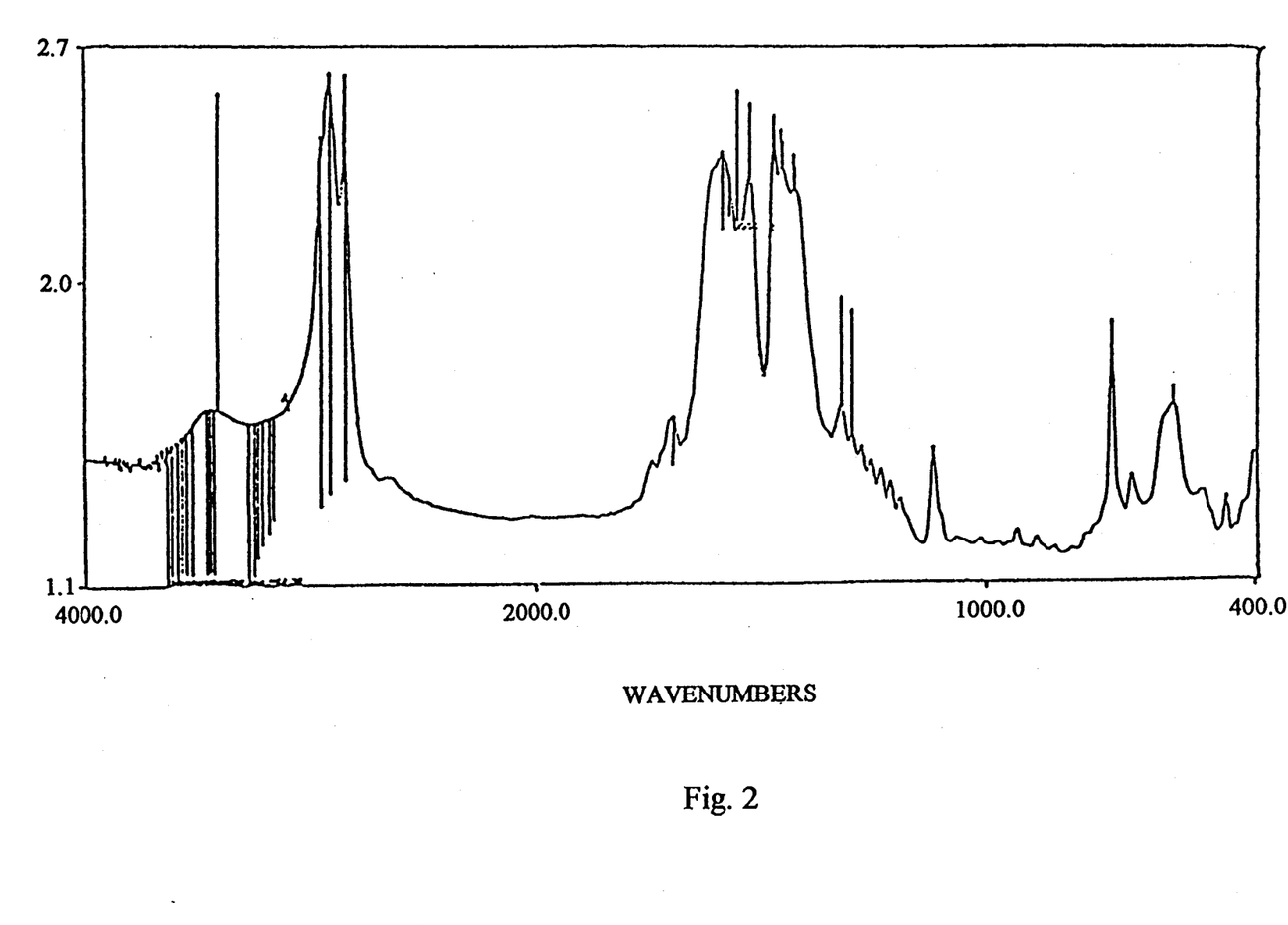
FIG. 2 is an FTIR spectrum of ferric stearate after the alternating alkalinization-acidization reaction of the invention.
Figure 3:
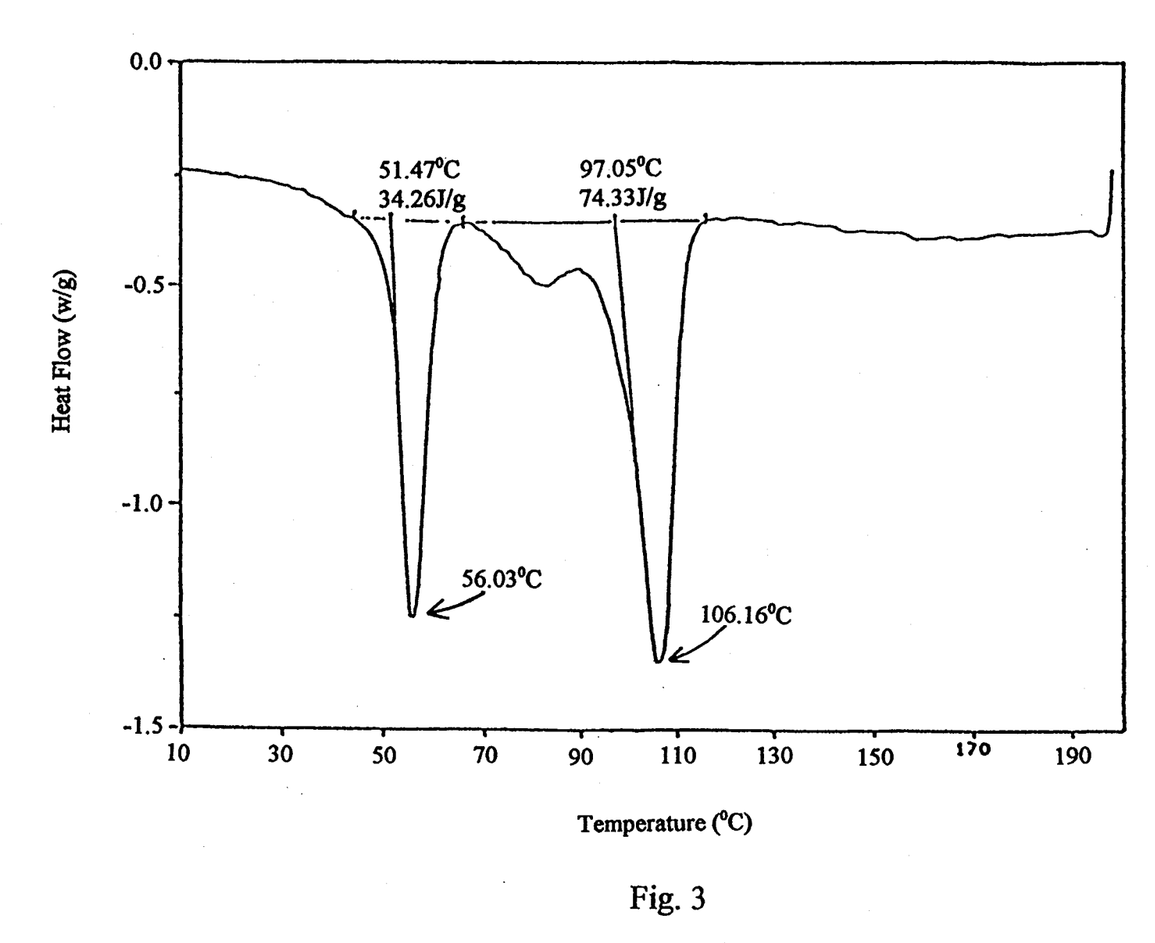
FIG. 3 is an DSC spectrum of ferric stearate before the alternating alkalinization-acidization reaction of the invention.
Figure 4:
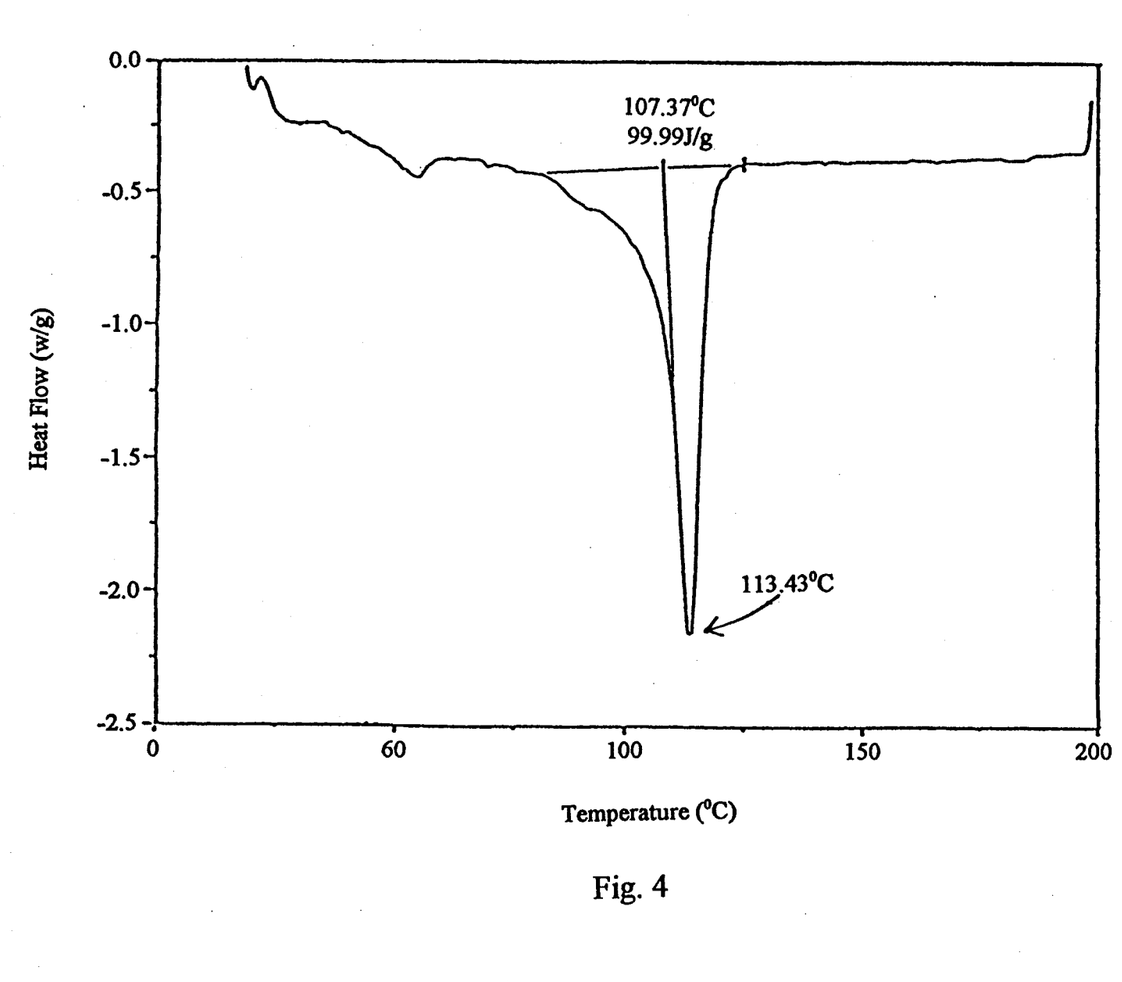
FIG. 4 is an DSC spectrum of ferric stearate after the alternating alkalinization-acidization reaction of the invention.

Reaction products before and after the alternating alkalinization-acidization reaction process were obtained and analyzed using a titration method. The amounts of stearic acid were 14.8% and 1.4%, respectively, before and after the alternating alkalinization-acidization reaction process. Table 1 shows a summary of the results, which clearly indicate a significant reduction in the residual fatty acid content by the treatment. The effectiveness of the present invention was also confirmed using the FTIR and DSC analysis, whose results were shown in FIGS. 1 through 4. Comparing the FTIR analysis results, which are shown in FIGS. 1 and 2, the disappearance of the stearic acid, which showed an absorption peak at 1,707 $cm^{-1}$, can be clearly observed. The DSC analysis results, which are shown in FIGS. 3 and 4, also clearly confirm the disappearance of the low-melting-point stearic acid.

EXAMPLE 2: PREPARATION OF CERIUM STEARATE 10 grams of sodium hydroxide was dissolved in 500 grams of water in a reaction bath. 75 grams of stearic acid (molecular weight=204) was added the solution. The solution was heated to a temperature of 90° C. to achieve a complete saponification of the stearic acid. The reaction product was a transparent gelatinous sodium stearate soap. 293 ml of ceric chloride solution (0.3M) was added to the sodium soap solution to initiate the double decomposition reaction. After the reaction product, which appeared in the form as a milky suspending agglomerate, was formed, water in the reaction bath was removed via filtration. This completes the initial portion of the synthesis reaction.

125 ml of 0.4M sodium hydroxide and 375 ml of water were into the reaction bath, which was then stirred and heated until its temperature reached 90° C. to effectuate a saponification of the unreacted residual stearic acid in the reaction product. Then 58.8 ml of acidic 0.3 ceric chloride solution was added to the reaction bath to cause additional ceric stearic acid salt to be formed which again was floating in the solution. This completed the first cycle of the alternating alkalinization-acidization reaction.

Two more cycles of the alternating alkalinization-acidization reaction were performed on the reaction products. The second cycle comprised the steps of adding 85.0 ml of 0.4M sodium hydroxide solution to cause saponification reaction, followed by the addition 21 ml of 0.3M ceric chloride to cause double decomposition reaction. In the third or the final cycle, 31 ml Of 0.4M sodium hydroxide solution was added to cause saponification, followed by the addition of 14.6 ml of 0.3M ceric chloride solution to complete the entire alternating alkalinization-acidization reaction process.

Figure 5:
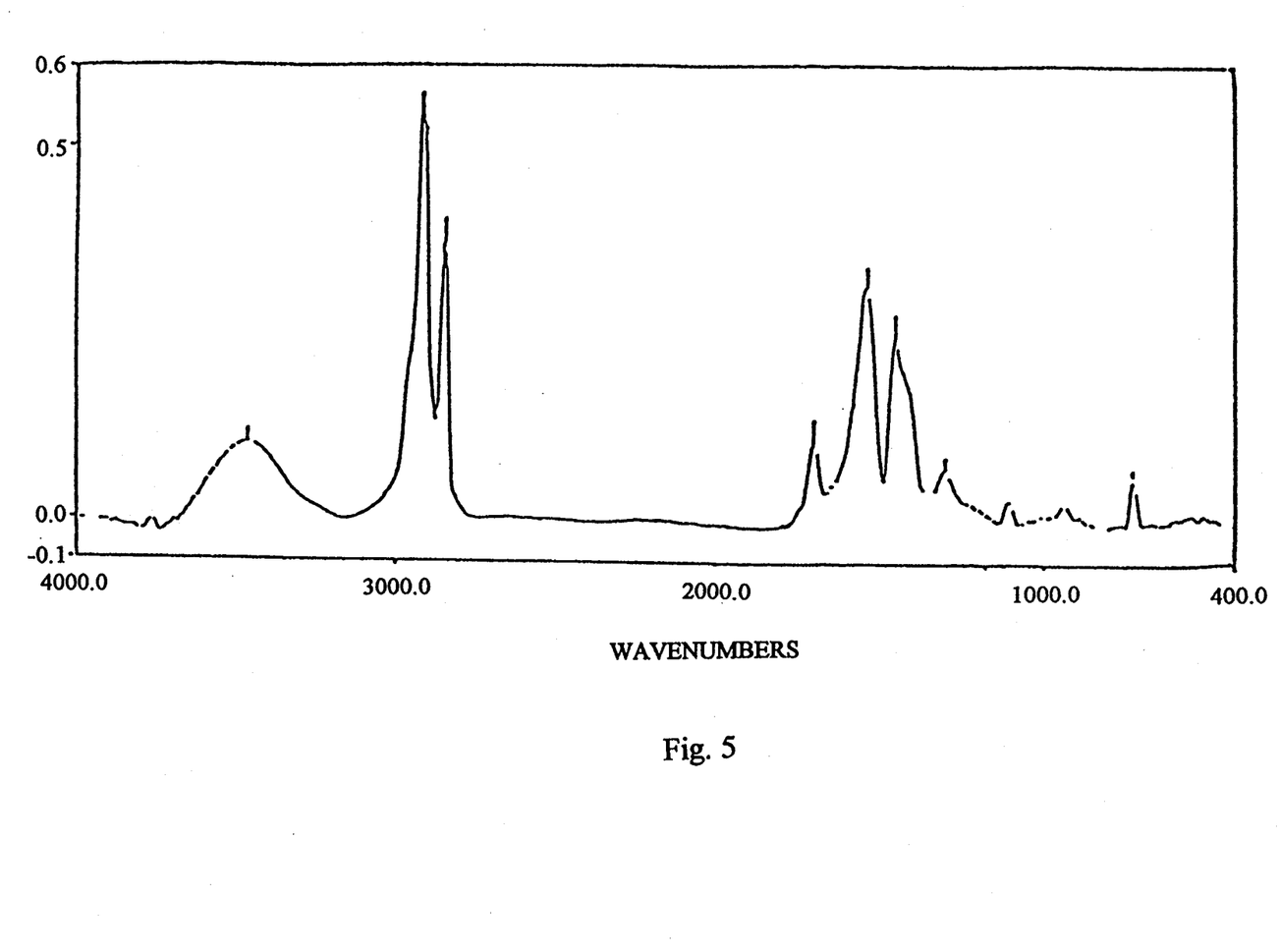
FIG. 5 is an FTIR spectrum of ceric stearate before the alternating alkalinization-acidization reaction of the invention.
Figure 6:
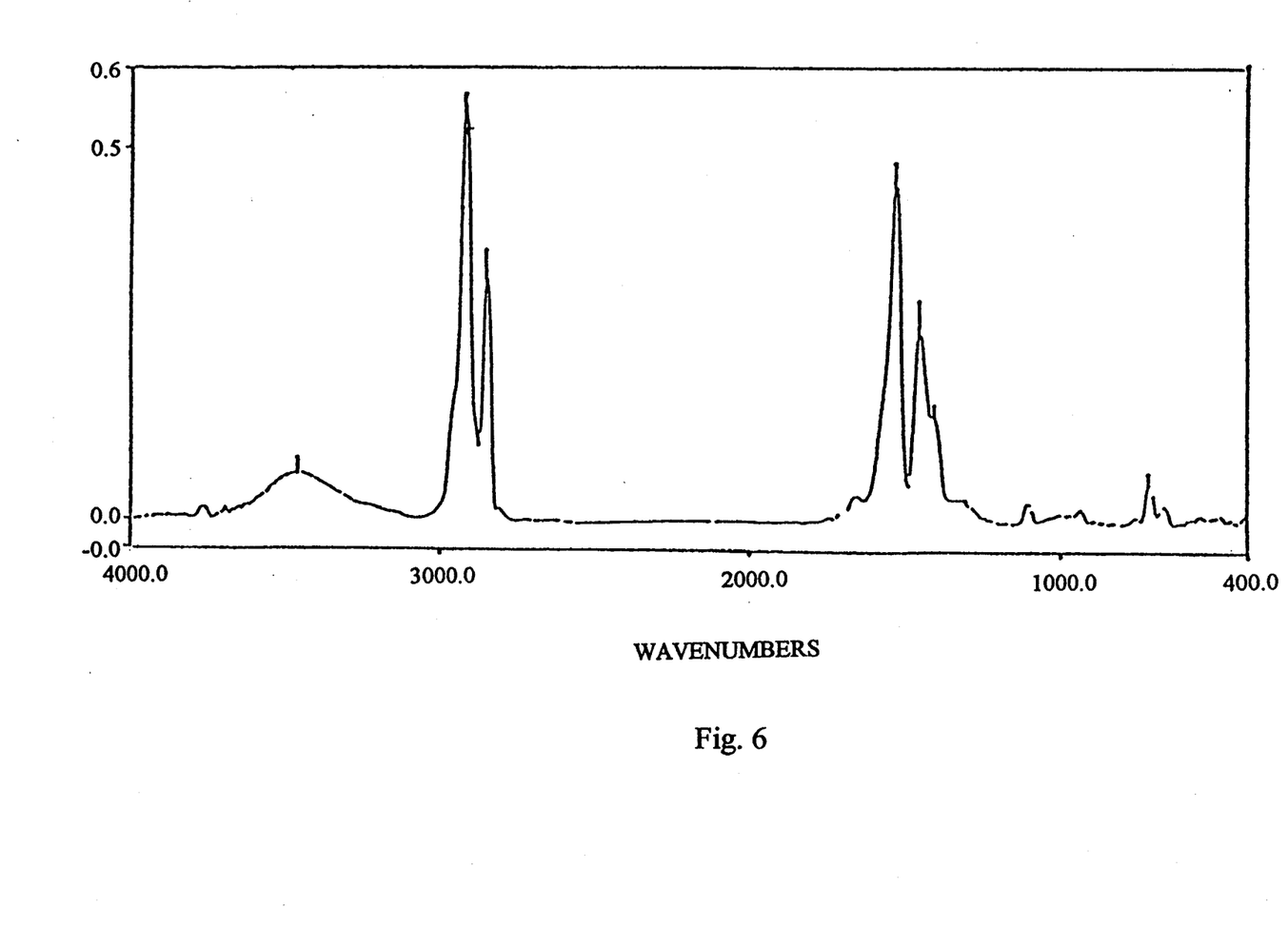
FIG. 6 is an FTIR spectrum of ceric stearate after the alternating alkalinization-acidization reaction of the invention.
Figure 7:
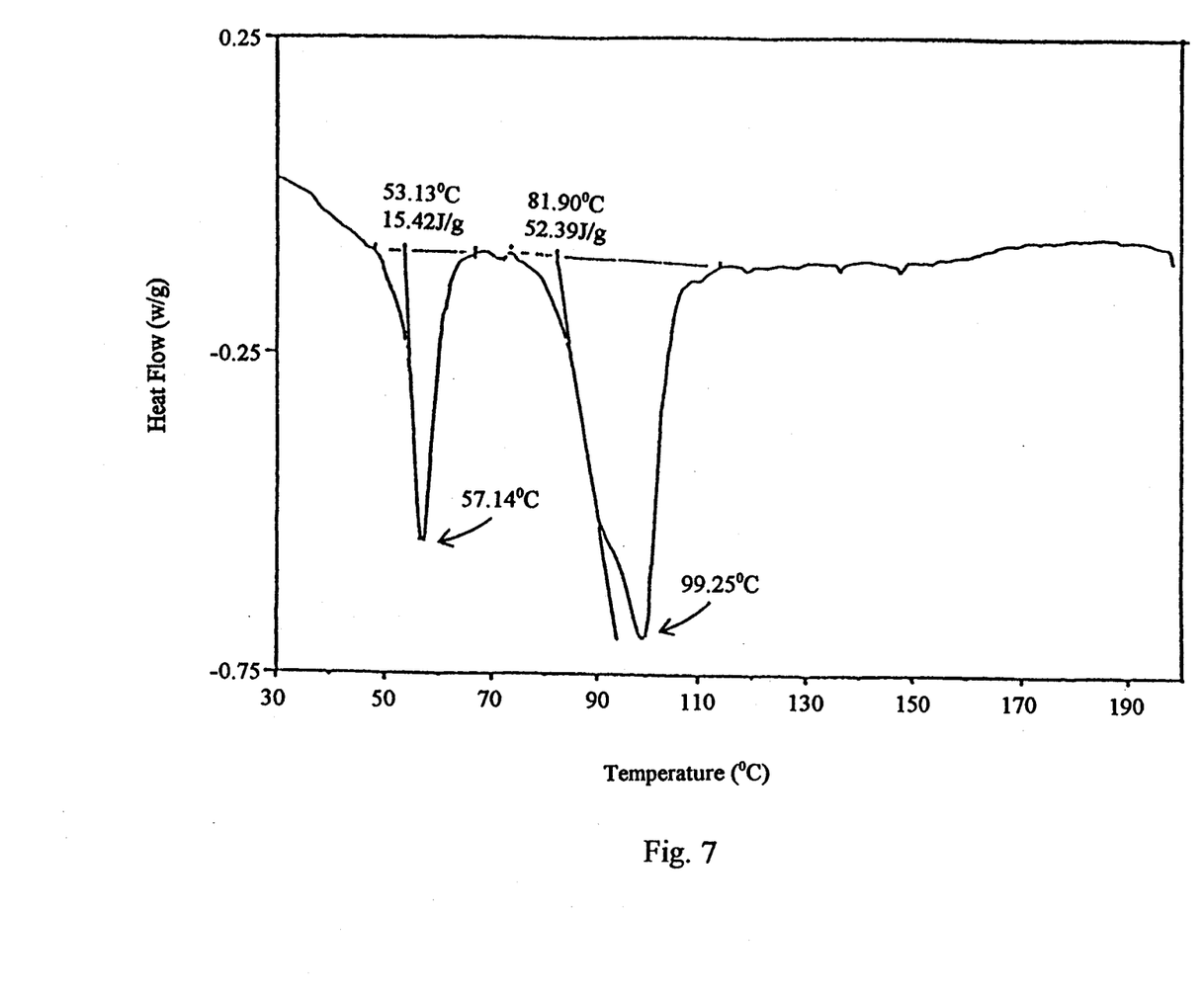
FIG. 7 is an DSC spectrum of ceric stearate before the alternating alkalinization-acidization reaction of the invention.
Figure 8:
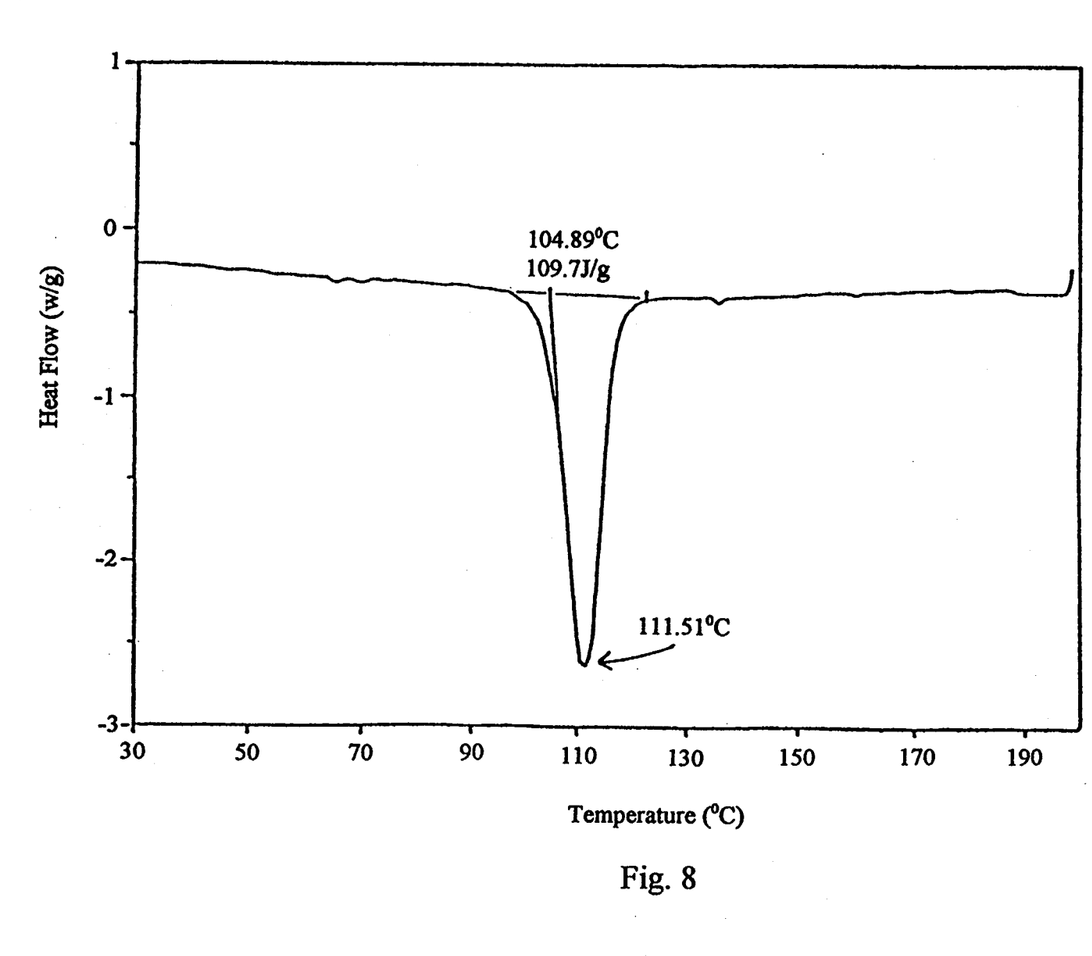
FIG. 8 is an DSC spectrum of ceric stearate after the alternating alkalinization-acidization reaction of the invention.

Reaction products before and after the alternating alkalinization-acidization reaction process were obtained and analyzed using a titration method. The amounts of stearic acid were 6.5% and 1.0%, respectively, before and after the alternating alkalinization-acidization reaction process. Table 1 shows a summary of the results, which clearly indicate a significant reduction of the residual fatty acid content after the treatment. The effectiveness of the present invention was also illustrated using FTIR and DSC analysis, whose results were shown in FIGS. 5 through 8. Comparing the FTIR results, which are shown in FIGS. 5 and 6, the disappearance of the stearic acid can be clearly confirmed. The DSC results, which are shown in FIGS. 7 and 8, also clearly demonstrate the disappearance of the low-melting-point stearic acid. The cerium ions that can be used in this process include $Ce^{+2}$, $Ce^{+3}$ and $Ce^{+4}$.

EXAMPLE 3

250 grams of metallic stearate salts each prepared from Examples 1 and 2 and were respectively blended with 4,750 grams of low density polyethylene (NA 207-66 from USI, Far East Corp.) and compounded using a double-roll mill at 140° C. for 5–10 minutes. This was followed by using dicing machine to cut the blends into small cubes which constituted a concentrated masterbatch of salt/PE having a stearate salt concentration of 5 PHR (parts per hundred parts resin). The concentrated salt/PE masterbatch was then mixed with PE at various proportions and conveyed to a blower (a 40 mm single screw extruder having an L/D ratio of 28:1) to make PE films having a thickness of about 0.03 –0.04 mm. Thus an enumeration of PE films containing different types of photolyzing agents prepared from the method of the present invention at various concentrations were available for performing a comparative study.

The blown PE films were placed under a xenon-arc radiation source for an accelerated and simulated weathering test. Appropriate light filters were placed before the xenon-arc radiation source so that its light intensity and spectral distribution resemble those of the natural sunlight. The sample PE films were placed 508 mm from the radiation source and were circled thereabout to achieve the desired result of uniform exposure. The humidity of the test environment was controlled at about 35±5% and the temperature at about 40° C. The PE film samples were observed on a daily basis to record the crack time. A shorter the crack time is an indication of faster rate of polymer photo-degradation.

Results from the accelerated weathering tests were summarized in Table 2, which enumerates crack times of PE films containing the two types of metallic stearate salts prepared from the above examples at various concentrations, including one sample that does not contain any stearate salt additives, exposed under the xenon-art radiation source. The crack time was reduced from over 1,000 hours for the films without the photolyzing agents to between 200–600 hours with the fatty acid salts. Table 2 clearly indicates that the ferric stearate and the ceric stearate prepared from the method of the present invention can be effectively used as excellent photolyzing agents to promote the photo-degradation of plastics. Table 2 also indicates that rate of the polymer photo-degradation time can be adjusted either by using various types of metallic fatty acid salts, or by controlling the amount of dosage thereof, or both.

The foregoing description of the preferred embodiments of this invention has been presented for purposes of illustration and description. It is not intended to limit the invention to the precise form disclosed. Obvious modifications or variations are possible in light of the above teaching. For example, appropriate metals constituting the metallic salts can be selected from the group consisting of iron, aluminum, cerium, cobalt, copper, manganese, magnesium, calcium, nicker, etc. And the cationic group constituting the metallic salt can be selected from the group consisting of chloride, sulfate, nitrate, acetate, etc, or mixture thereof. The embodiment was chosen and described to provide the best illustration of the principles of this invention and its practical application to thereby enable one of the ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

TABLE 1

| Metallic Fatty Acid Salt | Before alternating alkalinization-acidization reaction | After alternating alkalinization-acidization reaction |
|---|---|---|
| Ferric Stearate | 14.8% | 1.4% |
| Ceric Stearate | 6.5% | 1.0% |

TABLE 2

| Type of Metallic Fatty Acid and Concentration | Crack Time (Hours) |
|---|---|
| None | >1,000 hr |
| Ferric Stearate 0.03 PHR | 343 hr |
| Ferric Stearate 0.1 PHR | 300 hr |
| Ferric Stearate 0.25 PHR | 217 hr |
| Ferric Stearate 0.5 PHR | 217 hr |
| Ceric Stearate 0.03 PHR | 845 hr |
| Ceric Stearate 0.1 PHR | 670 hr |
| Ceric Stearate 0.25 PHR | 644 hr |
| Ceric Stearate 0.5 PHR | 550 hr |

What is claimed is:

1. A method for the preparation of high purity metallic salts of fatty acid which can be used as a photolyzing agent to promote photo-degradation of polymers, said method comprises the steps of:
   (a) reacting a fatty acid with an aqueous alkali hydroxide to cause a sponification reaction of said fatty acid and form an alkali soap;
   (b) mixing said alkali soap with an aqueous solution of a metallic salt at a pre-determined temperature to cause the production of a metallic fatty acid salt, said metallic salt containing an anion and a metallic ion to be included in said metallic fatty acid salt;
   (c) performing at least one cycle of the following alternating alkalinization-acidization reaction:
      (i) adding about 0.01 to 0.5 times the amount of said aqueous alkali hydroxide solution used in step (a) to said metallic fatty acid salt to raise solution pH; and
      (ii) adding an acidic aqueous solution containing said metallic ion, about 0.01 to 0.5 times of said aqueous metallic salt solution used in step (b) to a reaction mixture from step (i) to lower solution pH;
   (d) whereby said step (i) causes a saponification of unreacted residual fatty acids to alkali soap and said step (ii) causes formation and precipitation of said metallic fatty acids salts and completes a double decomposition of said alkali soap to form metallic salts of said fatty acid.

2. The method of claim 1 wherein said alkali hydroxide is sodium hydroxide and said alkali soap is sodium soap.

3. The method of claim 1 wherein said fatty acid has a carbon number of between about 6 to about 25.

4. The method of claim 1 wherein said steps (i) and (ii) are conducted at temperatures between about 60° C. to about 100° C.

5. The method of claim 1 wherein said steps (i) and (ii) are conducted at temperatures between about 80° C. to about 90° C.

6. The method of claim 1 wherein said metallic salt comprises at least one anion group and at least one cationic group, and said cationic group is selected from the group consisting of iron, aluminum, cerium, cobalt, copper, manganese, magnesium, calcium, nicker, and said anion group is selected from the group consisting of chloride, sulfate, nitrate, acetate, or mixture thereof.

7. The method of claim 1 wherein said saponification reaction between said fatty acid and said aqueous alkali hydroxide takes place at temperatures between about 60° C. to about 100° C.

8. The method of claim 7 wherein said temperature in step (b) is between about 80° C. to about 90° C.

9. A method for the removal of fatty acids from metallic salts of said fatty acid comprising the steps of:
   (a) adding an aqueous alkali hydroxide solution to said metallic fatty acid salt so as to raise solution pH and cause a saponification reaction of fatty acids contained in said metallic fatty acid salt to form an alkali soap;
   (b) adding an acidic aqueous salt solution of said metal to a reaction mixture from step (b) to lower solution pH and cause precipitation of additional amounts of said metallic salt of said fatty acid from said reaction mixture; and
   (c) repeating the steps of (a) and (b) if desired and/or necessary.

10. The method of claim 9 wherein said alkali hydroxide is sodium hydroxide.

11. The method of claim 9 wherein said fatty acid has a carbon number of between about 6 to about 25.

12. The method of claim 9 wherein said steps (a) and (b) are conducted at temperatures between about 60° C. to about 100° C.

13. The method of claim 9 wherein said steps (a) and (b) are conducted at temperatures between about 80° C. to about 90° C.

* * * * *